United States Patent [19]

Hansen et al.

[11] Patent Number: 4,716,903
[45] Date of Patent: Jan. 5, 1988

[54] STORAGE IN A PACEMAKER MEMORY

[75] Inventors: James C. Hansen, Denver; Tibor A. Nappholz, Englewood; Robert H. Whigham, Aurora, all of Colo.

[73] Assignee: Telectronics N.V., Curacao, Netherlands Antilles

[21] Appl. No.: 915,696

[22] Filed: Oct. 6, 1986

[51] Int. Cl.⁴ .............................................. A61B 5/04
[52] U.S. Cl. ............................ 128/419 PG; 128/695; 128/696; 128/419 P; 128/708; 375/28; 375/29; 364/569
[58] Field of Search ............. 128/419 P, 695, 696, 128/419 PG, 708; 375/28, 29; 364/569

[56] References Cited

U.S. PATENT DOCUMENTS

| 3,453,562 | 7/1969 | Magnuski | 375/29 |
| 4,071,825 | 1/1978 | McGuffin | 375/29 |
| 4,151,517 | 4/1979 | Kelly | 375/28 |
| 4,305,050 | 8/1985 | DeFreitas | 375/29 |
| 4,348,769 | 9/1982 | Kittel | 332/11 D |
| 4,466,440 | 8/1984 | Money et al. | 128/419 PG |
| 4,567,883 | 2/1986 | Langer et al. | 128/696 |
| 4,571,589 | 2/1986 | Slocum et al. | 128/419 PG |
| 4,614,192 | 9/1986 | Imran et al. | 128/419 PG |

Primary Examiner—Kyle L. Howell
Assistant Examiner—Timothy Keegan
Attorney, Agent, or Firm—Gottlieb, Rackman & Reisman

[57] ABSTRACT

An implantable pacemaker which stores in memory the representation of an ECG signal by compressing the data. Whenever the input signal changes by a threshold amount from the last time data was recorded, a representation of the time interval which has elapsed is recorded. In a maximimally efficient system, the only information which must be stored are the successive elapsed times, along with indications of when the input signal changes slope.

10 Claims, 1 Drawing Figure

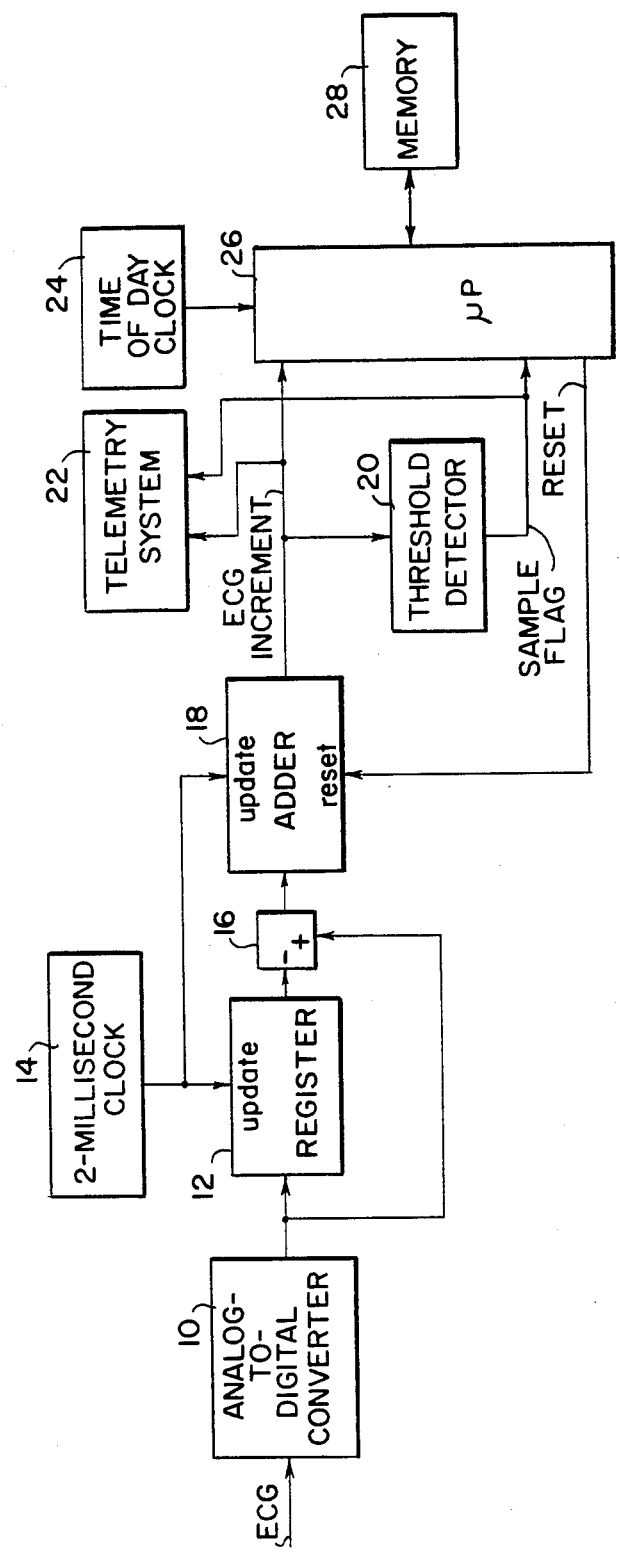

STORAGE IN A PACEMAKER MEMORY

DESCRIPTION

This invention relates to the storage in a pacemaker memory of electrocardiogram data, and more particularly to the storage of such data in compressed form.

A modern-day pacemaker processes an electrocardiogram (ECG) for a number of purposes. The ECG can be analyzed by the pacemaker for controlling its mode of operation, and it can be telemetered for diagnostic purposes. Also, data representative of the ECG can be stored in the pacemaker for subsequent analysis and/or telemetry. One problem with the storage of ECG data in a pacemaker is that the memory capacity of the pacemaker is limited.

It is a general object of our invention to provide for the storage of ECG data in compressed form, thereby reducing the memory requirements of a pacemaker.

Basic to an understanding of our invention is the realization that for most of a heartbeat cycle, the ECG waveform is steady-state. There is no need to store samples during the time period that the signal does not change.

Another observation of importance is that it is not really necessary even to store samples of the ECG waveform in order to reconstruct it later on. In delta modulation data compression systems, what are stored instead of samples are changes in successive samples. But it is not even necessary to store the changes. In accordance with the principles of our invention, every change is taken to be +1 or −1. All that is necessary in order to store magnitude information is to store the direction of the change from one sample to the next. What distinguishes one waveform from another is the time which elapses between successive changes of +1 or −1. The key information which is stored in the practice of our invention is the time which elapses between successive changes of predetermined magnitudes.

It is the type of information which is important, not the detailed form which the data takes. The data can be compressed even further by storing not the actual time of day by which a predetermined change in the signal amplitude has occurred, but rather the change in the time of day since the preceding storage. This is a form of delta modulation, applied to the storage of time information rather than amplitude information. Furthermore, since an ECG waveform increases or decreases monotonically most of the time, instead of storing with each piece of time data whether the amplitude change is positive or negative, all that has to be done is to store a flag with only those pieces of time data which are associated with a change in the slope of the ECG signal. In its most refined form, the data storage consists of nothing more than elapsed times, each elapsed time corresponding with a predetermined amplitude change, with the occasional storage of a new direction of input signal change.

This is not to say that when utilizing our invention amplitude information (preferably in delta modulation form) should never be stored. On the contrary, there are cases in which this will be necessary. For example, when the input signal changes by a predetermined amount in either direction, ideally what is necessary is the storage of the time which has elapsed since the last storage. However, the microprocessor employed to sample the signal and store the data may not be fast enough, especially if it has other tasks to perform. When the input signal passes the "change" threshold level in either direction, an interrupt may be furnished to the microprocessor. However, by the time the microprocessor actually responds to the interrupt, the input signal may have changed and more time may have elapsed. Consequently, when the response time of the microprocessor is slow, what should be stored is not until the time which has elapsed from the last storage not until the time of the interrupt, but rather until the time of the microprocessor's response to the interrupt. By this time, however, the input signal may have changed more than the predetermined increment, and thus along with the time change data the amplitude change data should also be stored.

Because the stored data characterizes the input signal, the input signal can be reconstructed from it—either by the microprocessor or, if the pacemaker telemetry system transmits the data to an external processor, then by the external processor. Each sample which is stored consists of time-change information, and thus the time at which each sample occurs can be noted on the time axis. If the response of the microprocessor to an interrupt request is instantaneous, all that is necessary to reconstruct the signal is to determine the change in direction of the signal a few times during each cycle when the appropriate flag is stored. Otherwise, every sample is one increment greater or less than the preceding sample. If the microprocessor response is not instantaneous, then each time-change value has associated with it an amplitude-change value, and each pair of values represents another data point in the reconstructed signal.

Further objects, features and advantages of our invention will become apparent upon consideration of the following detailed description in conjunction with the drawing which depicts the illustrative embodiment of our invention.

Only those parts of the pacemaker are shown in the drawing which are necessary for an understanding of the present invention. For example, the pulse generating circuitry is not shown.

The ECG signal is applied to the input of analog-to-digital converter 10, and the output of this block is extended to the input of register 12. Register 12 stores a new digital sample every time that its update input is pulsed by the 2-millisecond clock 14. Subtractor 16 forms the difference between the new sample and the old, and the difference is applied to the input of adder 18. Register 12 and subtractor 16 together are the equivalent of a digital differentiator. The update input of the adder is similarly clocked at intervals of 2 milliseconds, and thus the output of the adder represents the sum of a series of sample differences. The sum is the total increment (or decrement) of the ECG signal since the last time that the adder was reset.

The output of adder 18 is applied to the input of threshold detector 20. The threshold detector generates a sample flag to the microprocessor 26 whenever the ECG increment, the change in the ECG signal since the last time that the adder was reset, exceeds the threshold level in either direction. If telemetry system 22 functions in real time, as opposed to the storage of data in memory 28 and its subsequent transmission to an appropriate receiver, the telemetry system may transmit the ECG increment whenever the sample flag signal is generated. It is not always necessary to transmit the value of the ECG increment since its absolute value will always be equal to the threshold level. All that is necessary is to transmit an indication of the polarity of the increment. The ECG signal can be reconstructed from equal increments, provided that time-base information is known; the time-base information is representd by the time of each transmission.

The main purpose of the invention, however, is to allow a representation of the ECG signal to be stored in the memory for subsequent reconstruction. [That subsequent reconstruction may be via the telemetry system, but at a time when communication has been established and which may be other than when the data representative of the ECG signal is being recorded.] A time of day clock 24 is applied to an input of the microprocessor. Whenever a sample flag is present, the microprocessor stores data representative of the time of day. Instead of storing the actual time of day, reduced storage is possible if what is stored is a smaller number which represents the time which has elapsed since the generation of the last sample flag. When the time of day representation is stored in memory 28 by the microprocessor, the microprocessor generates a reset signal so that the adder will be reset. As mentioned above, the only information which must be stored in addition to time information is the direction of the signal change. Since every piece of amplitude change data has an absolute value which is equal to the threshold level, it is not necessary to store that absolute value. It is sufficient to store the direction of the change in the input signal whenever a sample flag is generated, and it is even possible to reduce this minimal amount of storage by storing amplitude information which simply represents a change in the slope of the input signal whenever such a change occurs with the generation of a current sample flag.

As mentioned above, it may be that the microprocessor cannot respond instantaneously to a sample flag. In such a case, a non-negligible amount of time may elapse between the generation of a sample flag and the generation of a reset pulse by the microprocessor, and the ECG increment may have changed and may no longer be equal to the threshold level. Consequently, where the response of the microprocessor is not instantaneous, in addition to time-of-day (or the equivalent elapsed time) information storage, it is necessary to store amplitude change data. To reduce the amount of memory required, all that should be stored are the successive ECG increments. In a polled system, the sample flag would not generate an interrupt and it might be quite a few milliseconds before the microprocessor actually examines the sample flag input to discover that a new sample is available. In such a system it is certainly preferable to store amplitude information.

It will be apparent that by utilizing the pacemaker memory in the efficient manner described above, the pacemaker can actually function as a Holter monitor. A key to the reduced storage is the selection of an appropriate threshold for detector 20. The threshold should be high enough so that minor, information-unimportant, changes in the cardiac signal do not result in the generation of sample flags. In this way, no memory storage is required for most of the cardiac signal which is of little interest anyway.

Although the invention has been described with reference to a particular embodiment it is to be understood that this embodiment is merely illustrative of the application of the principles of the invention. Numerous modifications may be made therein and other arrangements may be devised without departing from the spirit and scope of the invention.

We claim:

1. In an implantable pacemaker having means for sensing a cardiac signal, a system for storing a representation of said signal from which the signal subsequently may be reconstructed comprising means for monitoring said signal and determining each time at which the signal has changed by at least a threshold value since the preceding time at which the signal similarly changed, memory means, and means for storing in said memory means data indicative of the intervals between successive times at which said signal changed by at least said threshold value.

2. An implantable pacemaker in accordance with claim 1 wherein all of the signal changes are equal.

3. An implantable pacemaker in accordance with claim 1 wherein the signal changes may be unequal in value, and for each interval for which data is stored in said memory means said storing means further stores data indicative of the magnitude of the signal change associated with such interval.

4. An implantable pacemaker in accordance with claim 1 further including telemetring means, and means for operating such telemetring means at each time the signal changes by at least said threshold value.

5. An implantable pacemaker in accordance with claim 1 wherein said threshold value is large enough such that no data is stored for most of said cardiac signal.

6. A method for storing in an implantable pacemaker a representation of a sensed cardiac signal from which the signal subsequently may be reconstructed comprising the steps of monitoring said signal and determining each time at which the signal has changed by at least a threshold value since the preceding time at which the signal similarly changed, and storing in a memory data indicative of the intervals between successive times at which said signal changed by at least said threshold value.

7. A method in accordance with claim 6 wherein all of the changes are equal.

8. A method in accordance with claim 6 wherein the changes may be unequal in value, and for each interval for which data is stored in said memory there is further stored data indicative of the magnitude of the change associated with such interval.

9. A method in accordance with claim 6 further including the step of transmitting a signal at each time that said signal changes by at least said threshold value.

10. A method in accordance with claim 6 wherein said threshold value is large enough such that no data is stored for most of said cardiac signal.

* * * * *